US008978645B2

(12) United States Patent
Chen

(10) Patent No.: US 8,978,645 B2
(45) Date of Patent: Mar. 17, 2015

(54) DRY POWDER AEROSOLIZED INHALER

(75) Inventor: Qingtang Chen, Nanjing (CN)

(73) Assignees: Qingtang Chen, Zhejiang (CN); Xin Chen, Jiangsu (CN)

( * ) Notice: Subject to any disclaimer, the term of this patent is extended or adjusted under 35 U.S.C. 154(b) by 1336 days.

(21) Appl. No.: 11/887,755

(22) PCT Filed: Mar. 13, 2006

(86) PCT No.: PCT/CN2006/000381
§ 371 (c)(1),
(2), (4) Date: Oct. 2, 2007

(87) PCT Pub. No.: WO2006/105709
PCT Pub. Date: Oct. 12, 2006

(65) Prior Publication Data

US 2009/0025720 A1 Jan. 29, 2009

(30) Foreign Application Priority Data

Apr. 4, 2005 (CN) .......................... 2005 1 0038681

(51) Int. Cl.
*A61M 15/00* (2006.01)
*B65D 83/06* (2006.01)

(52) U.S. Cl.
CPC ....... *A61M 15/0028* (2013.01); *A61M 15/0015* (2014.02); *A61M 15/0021* (2014.02); *A61M 2202/064* (2013.01); *A61M 2206/14* (2013.01)
USPC ............. 128/203.15; 128/203.23; 128/203.12

(58) Field of Classification Search
USPC ............. 128/200.24, 203.12, 203.15, 203.19, 128/203.21, 200.14–200.23
See application file for complete search history.

(56) References Cited

U.S. PATENT DOCUMENTS

| | | | | |
|---|---|---|---|---|
| 5,301,666 | A | 4/1994 | Lerk et al. | |
| 5,349,947 | A * | 9/1994 | Newhouse et al. | 128/203.21 |
| 5,437,270 | A * | 8/1995 | Braithwaite | 128/203.15 |
| 5,724,960 | A * | 3/1998 | Bruna | 128/203.15 |
| 6,182,655 | B1 * | 2/2001 | Keller et al. | 128/203.15 |

(Continued)

FOREIGN PATENT DOCUMENTS

| | | |
|---|---|---|
| CN | 1074381 A | 7/1993 |
| CN | 1255869 A | 6/2000 |

(Continued)

OTHER PUBLICATIONS

International Search Report, dated Jun. 20, 2006, corresponding to PCT/CN2006/000381.

*Primary Examiner* — Valerie L Skorupa
(74) *Attorney, Agent, or Firm* — Christie, Parker & Hale, LLP

(57) ABSTRACT

This invention provides an aerosolized inhaler which enables the drug powder to aerosolize within the inhaler by breathing in the air, comprising the main body (11) and the mouthpiece connector (12) connected thereupon, wherein the inhaler the main body (11) has drug holding opening (1), which connects with the vortex passage, and the vortex passage connects with the mouthpiece (9) on the mouthpiece connector (12). It has many obvious advantages as increasing the inhalation rate, pushing more drug granule to reach to the lower respiratory tract and even into the alveolus; and meanwhile, keeping the drug from being blown out of the inhaler when the users breathes out, preventing from cross inflection and minimizing the side effect of the drug to the whole body, and obviously lightening the burden on the users.

10 Claims, 3 Drawing Sheets

(56) References Cited

U.S. PATENT DOCUMENTS

| | | |
|---|---|---|
| 6,273,086 B1 * | 8/2001 | Ohki et al. ............... 128/203.21 |
| 6,347,629 B1 | 2/2002 | Braithwaite |
| 6,371,111 B1 * | 4/2002 | Ohki et al. ............... 128/203.15 |
| 7,246,617 B1 * | 7/2007 | Harmer et al. ............ 128/203.15 |
| 7,521,069 B2 * | 4/2009 | Patton et al. .................. 424/499 |
| 7,708,011 B2 * | 5/2010 | Hochrainer et al. ...... 128/200.14 |
| 2002/0073997 A1 * | 6/2002 | Keane et al. ............. 128/203.21 |
| 2003/0164169 A1 * | 9/2003 | Stangl et al. ............. 128/203.12 |
| 2004/0182387 A1 * | 9/2004 | Steiner et al. ............ 128/203.15 |
| 2005/0183723 A1 * | 8/2005 | Pinon et al. ............... 128/203.15 |

FOREIGN PATENT DOCUMENTS

| | | |
|---|---|---|
| CN | 2391625 Y | 8/2000 |
| CN | 1437551 A | 8/2003 |
| JP | 9-248342 | 9/1997 |
| WO | WO 99/39761 | 8/1999 |
| WO | WO 01/98174 A1 | 12/2001 |

\* cited by examiner

DRY POWDER AEROSOLIZED INHALER

CROSS-REFERENCE TO RELATED APPLICATION

This application is a National Phase Patent Application of International Patent Application Number PCT/CN2006/000381, filed on Mar. 13, 2006, which claims priority of Chinese Patent Application Number 200510038681.1, filed on Apr. 4, 2005.

FIELD OF THE INVENTION

This invention relates to a kind of medical appliance, particularly, the dry powder inhaler, which is specified in detail as a dry powder aerosolized inhaler to aerosolize the drug powder.

BACKGROUND ART

At present, dry powder inhalers available have many forms of structure, but there are three main problems like: firstly, the low inhalation rate, which is, after the research on it, only 8~16% of the drug granule is delivered to airways and lungs; secondly, the dry powder being easily blown out of the appliance, in case when breathing out into the mouthpiece, around where there are some dry powders for the inhaler to be breathed in, especially, the elderly and young children will often fail to control their expiration so as to blow out the dry powder; and thirdly, some mouthpieces are not easily cleaned, and particles of powder residue that have accumulated on the mouthpiece might cause cross inflection.

SUMMARY OF THE INVENTION

This invention is intended to design a new dry powder aerosolized inhaler which increases inhalation rate of the drug obviously and allows more drug granule to reach to the lower respiratory tract and the alveolus by aerosolizing the drug powder in the inhaler with the breathed-in airflow; meanwhile, keeps the drug from being blown out of the appliance when users breathe out, prevents from the cross inflection and reduces side effects to the whole body by the drug, and greatly lighten the economic burden on the users.

The technical scheme of this invention is:

A dry powder aerosolized inhaler, including main body 11 and attached mouthpiece connector 12, characterized in that in the main body 11, there is the drug holding opening 1, which connects the vortex passage, and which connects the mouthpiece 9 to the connector 12.

This invention further takes the following technical measures:

The mentioned drug holding opening 1 can be funnel-shaped one, and above the said funnel-shaped drug holding opening 1, there is a cover slab 2 mounted on the main body 11.

On the said cover slab 2 to drug holding opening, there are small openings.

On the main body 11, provided with air intake 4, and the air intake 4 is connected with funnel-shape drug holding opening 1 through air inlet channel 5.

The main body 11 at the said air intake 4 is fixed with a single direction valve plate 3.

When the number of the said vortex passages is more than one, the vortex passages can be connected in series or in parallel.

When the number of the said vortex passages is two or more, the vortex passages could be partly connected in series or partly in parallel.

The vortex passage consists of small inside diameter air inlet channel 6, large inside diameter vortex chamber 7 and small inside diameter air outlet channel 8; one end of the small inside diameter air inlet channel 6 is connecting with the large inside diameter vortex chamber 7, and the other end is connecting with drug holding opening 1; the large inside diameter vortex chamber 7 might connect directly with small inside diameter air outlet channel 8, or with the small inside diameter air inlet channel of the neighbor vortex passage; and follow this rule, until the small inside diameter air outlet channel in the last vortex passage connects with mouthpiece 9.

The joint of the above-mentioned large inside diameter vortex chamber 7 and small inside air inlet channel 6 is a structure of gradual change or of abrupt change.

The mouthpiece connector 12 is equipped with external casing 10 for user to keep in mouth, and there are many specifications of external casing for alternative uses.

BENEFICIAL EFFECT OF THIS INVENTION

1. Aerosolizing the inhaled drug granules before they enter the respiratory tract to increase the inhalation rate, and enable the drug powder to reach to the lower respiratory tract and the alveolus, so as to provide a more effective way of drug administration directly in the guarding against the respiratory tract diseases.

2. Keep powder from being blown out of the inhaler.

3. The mouthpiece external casing is cleaned easily to prevent the cross inflection.

4. There is a long mouthpiece external casing designed to the inhaler, and it can be stretched to the middle backward part of the mouth and align the mouthpiece to the throat, reducing the adhesion of the powder to the tongue or oral mucosa. In this way, it can help to improve the inhalation rate of powder, keep the oral mucosa and tongue from over-inhaling drug, and minimize the incidence of side effects of drug to the whole body.

DETAILED DESCRIPTION OF THE INVENTION

The invention will be further described by way of example accompanying drawings.

Example 1

As shown in FIG. 1-4.

Figure 1:
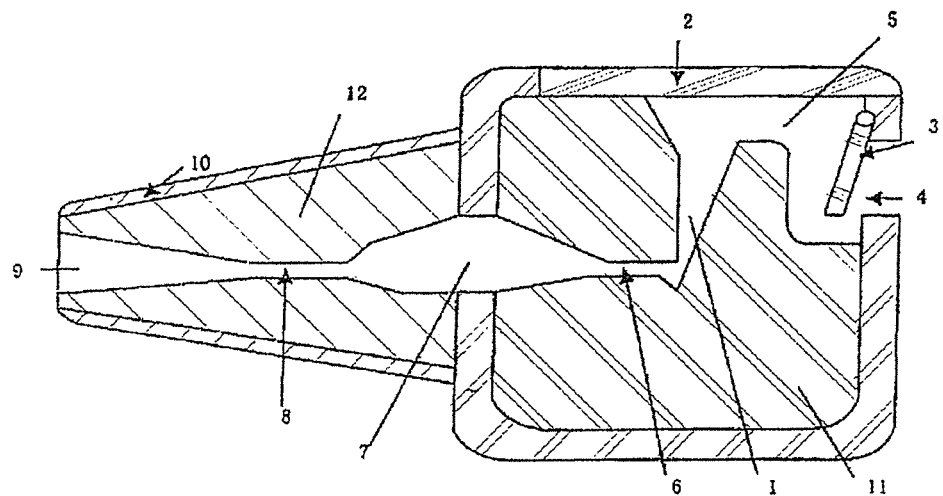
FIG. 1 is a scheme of structure of Example 1 of the present invention.
Figure 2:
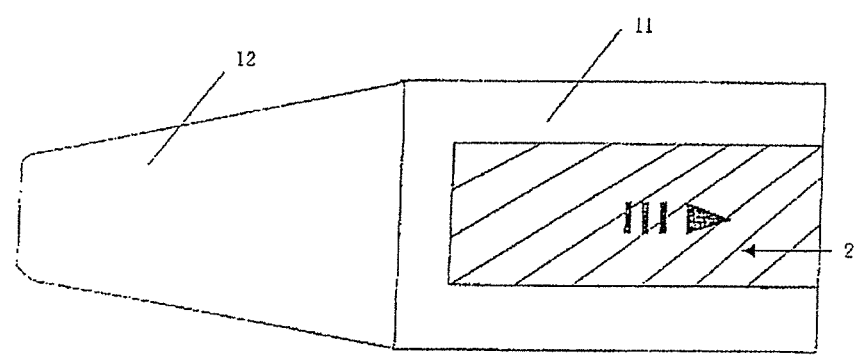
FIG. 2 is a vertical view of FIG. 1.
Figure 3:
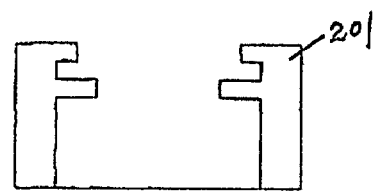
FIG. 3 is a schematic graph of structure of the slot to which the drug holding opening cover slab 2 of the main body fixed of Example 1 of the present invention.
Figure 4:
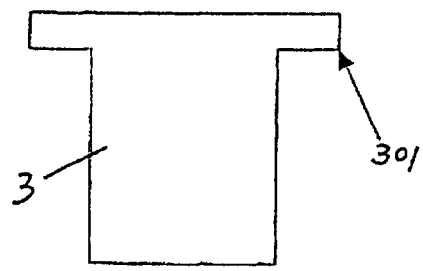
FIG. 4 is a scheme of structure of valve plate 3 of Example 1 of the present invention.

A kind of dry powder aerosolized inhaler is consisted of main body 11 and mouthpiece connector 12 connecting to the main body. And in the main body 11, there is a funnel-shaped drug holding opening 1, above which, there is a cover slab 2 on the main body 11 to the drug holding opening. And the cover slab 2 is fixed into the slot in main body 11, shown as FIG. 3, FIG. 3 is the scheme of cover slab 2 and cover slab slot 201 of this dry powder aerosolized inhaler. There could be some relevant small openings in the drug holding opening cover slab 2, and the funnel-shaped drug holding opening 1 connects with air inlet channel 5 in main body 11 and air inlet channel 6 of vortex passage respectively; and one end of the air outlet channel 8 connects with the mouthpiece 9 in the connector 12, to form a vortex passage. The main body 11 is provided with a single direction valve plate 3 at the position of the air inlet 4. FIG. 4 is the scheme of valve plate 3 and valve rings 301. The vortex passage is composed of small inside diameter air inlet channel 6, large inside diameter vortex chamber 7 and small inside diameter air outlet channel 8; and the small inside diameter air inlet channel 6 is connecting with the funnel-shaped drug holding opening 1 and the large inside diameter vortex chamber 7 respectively. If there are more than one vortex passages, the small inside diameter air outlet channel 8 in FIG. 1 corresponds to the small inside diameter air inlet channel 6, and it communicates with the large inside diameter vortex chamber in the neighbor vortex passage, and following this rule, until the last small inside diameter air outlet channel connects with mouthpiece 9. Mouthpiece 9 can take its structure as gradual change as shown in FIG. 1, or take its structure as abrupt change. The joint of the large inside vortex chamber 7 and the small inside air inlet channel 6 and the small inside air outlet channel 8 is a structure of gradual change as shown in FIG. 1 or a structure of abrupt change. The mouthpiece connector 12 is equipped with external casing 10 for user to keep in mouth, and there are many specifications of external casing 10 for alternative uses.

When applying, it could be made of injecting mould, or other materials like wood and ceramic. Mouthpiece connector 12 and main body 11 can be finished separately, and then assembled into a completed appliance; the main body is finished by dividing it into two parts at its vertical section, and then folding the separated two parts into one. The mouthpiece can be made part by part, and finally assembled with screws.

When specifically applying this invention, following methods can be applied:

First of all, assemble a funnel-shaped drug holding opening 1 with the inside diameter of 10 mm for its upper open, and 3 mm for its lower open, onto the main body 11 of the dry powder aerosolized inhaler. The bottom of this funnel-shaped drug holding opening 1 connects with the back passage structure of the drug holding opening. The side wall of the funnel-shaped drug holding opening 1 can be connected to the front passage (air inlet channel 5) of the drug holding opening; the air inlet channel 5 can be composed of several small gaps at width of 1 mm to filtrate the foreign matter in the air. The funnel-shaped drug holding opening 1 can be covered by the cover slab 2, which has some small openings with inside diameter of 3 mm; the cover slab 2 can also be without any opening. A pushing-pulling style cover slab is also applicable, which should be assembled into the cover slab slot of the drug holding opening, as shown in FIG. 3.

Secondly, the passage (the back passage of drug holding opening) between the bottom of funnel-shaped drug holding opening 1 and the mouthpiece can be used for dry powder aerosolized chamber (namely the vortex passage), and inside this passage, a short part of the small inside diameter air inlet channel 6 connects with a part of the large inside diameter passage (namely the vortex passage chamber 7) and the small inside diameter air outlet channel 8 to build up a construction unit. When the airflow goes into the large inside diameter passage (namely the vortex passage chamber 7) through the small inside diameter air inlet channel 6, it forms a vortex; and when the dry powder passes the vortex with the airflow, it aerosolizes entirely to form an aerosol. If there are two or more vortex channels in series or in parallel inside the passage, the dry powder is dispersed repeatedly to make it more aerosolized; the inside diameter of small inside diameter air inlet channel 6 can be around 3 mm, and the length of this part of the passage can be around 8 mm. The inside diameter of large inside diameter passage (namely vortex passage chamber 7) can be around 10 mm; the diameter of the air inlet channel of the large inside diameter passage (namely the vortex passage chamber 7) can be of either gradual change or abrupt change structure, and the latter has better efficiency of vortex. Then the inside diameter of the large inside diameter vortex chamber 7 is decreasing gradually, or keeps unchanged at full length, to avoid the dry powder from detention. The length for this passage can be around 25 mm.

Thirdly, to keep the powder from being blown out, the cover slab 2 on the upper of the funnel-shaped drug holding opening 1 shall have no opening, and after filling the drug, the cover slab 2 should shut at once. The side wall of the funnel-shaped drug holding opening 1, connects with the air inlet 4 through air inlet channel 5, and at the air inlet 4 there provided a single direction valve plate 3. When inhaling the air via mouthpiece 9, the valve plate 3 opens towards inside to allow the air in; in case when user breathes out into the mouthpiece 9, the valve plate 3 will close up lest the dry powder shall be blown out. The single direction valve plate 3 is assembled with the valve ring 301 in the valve ring holes on the main body 11, referring to FIG. 4. The air inlet 4 can be clogged by the valve plate to keep the valve plate from opening too wide.

Fourthly, external casing 10 is designed to attach the mouthpiece 12, so as to avail cleaning and sterilizing after use. The external casing 10 can be around 80 mm in length, and the part of the external casing to be kept in user's mouth can be of different sizes so that to offer choices to the users with different mouth sizes. A small protuberance can be made at the bottom side of the external casing 10, and it helps fix the external casing 10 when interlocking with the small whorl on the corresponding place on main body 11.

The applying process of this invention:

Feed dry powder (usually 1-3 cube mm) into the funnel-shaped drug holding opening, and shut the cover slab 2, and then finish the preparation before inhalation. When breathing in at mouthpiece 9, the valve plate 3 at air inlet 4 opens, and from which the air flows into the funnel-shaped drug holding opening 1 through the air passage 5. At the same time, the dry powder in the funnel-shaped drug holding opening 1 enters the air inlet channel 6 with the airflow, then to the large inside diameter vortex chamber 7, then the small inside diameter air outlet channel 8, and finally reaches to the oral cavity via mouthpiece 9. When the airflow enters the large inside diameter vortex chamber 7 and mouthpiece 9 and the oral cavity, a vortex has come into being to bring all the dry powder evenly suspending in the airflow, so as to form an aerosol. The mouthpiece connector 12 and the external casing 10 can be put in the middle of the oral cavity on the tongue with mouthpiece towards the throat, so as to decrease the adhesion of the powder to the oral mucosa and tongue. With the action as breathing in, the aerosolized powder can go widely and deeply into the lower respiratory tract and to the alveoli of the lungs. It shows entirely the advantages as small dosage, quick action, and minimized side effect to the whole body.

Example 2

Figure 5:
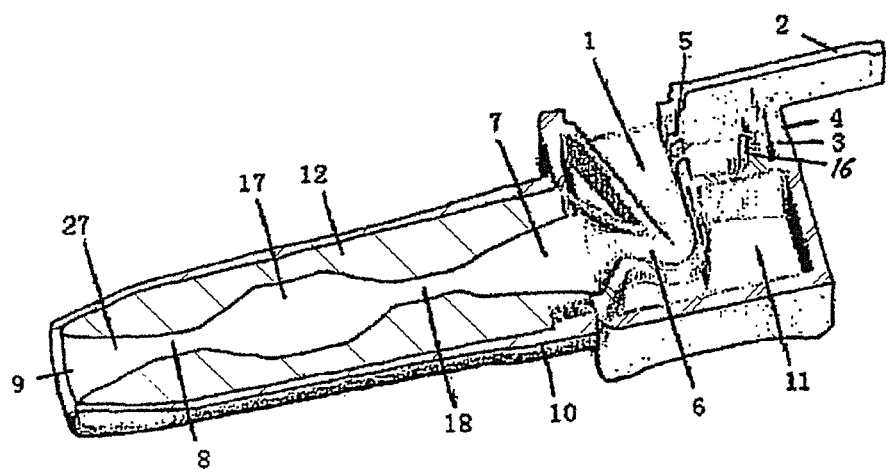
FIG. 5 is a scheme of structure of Example 2 of the present invention.

As shown in FIG. 5.

The dry powder aerosolized inhaler used in this example consists of main body 11 and mouthpiece connector 12 connected thereupon. And in the main body 11, provided with funnel-shaped drug holding opening 1, above the funnel-shaped drug holding opening 1, there is a cover slab 2 on the main body 11 to the drug holding opening. The cover slab 2 is fixed into the slot in 201 main body 11, and the funnel-shaped drug holding opening 1 connects with air inlet channel 5 in main body 11 and air inlet channel 6 of vortex passage respectively, and the small inside diameter air inlet channel 18 connects with the large inside diameter vortex chamber 7 and the large inside diameter vortex chamber 17 respectively, and one end of the small inside diameter air outlet channel 8 connects with the mouthpiece 9, and therefore, this example is in fact taking a mode of series-wound of two vortex passages which are represented by the large inside diameter vortex chamber 7, the large inside diameter vortex chamber 17 respectively. A single direction valve plate 3 is assembled at the air inlet 4, inside which there is a valve plate bar 16, preventing the valve plate from over-opening. The mouthpiece connector 12 is attached with external casing 10 for user to keep in mouth, and a small protuberance can be made at the inside bottom of the external casing 10, and it helps fix the mouthpiece 10 when interlocking with the small whorl on the corresponding place on main body 11. When breathing in at mouthpiece 9, the valve plate 3 at air inlet 4 opens automatically, and the airflows into the funnel-shaped drug holding opening 1 through the air passage 5, and allows the dry powder in the funnel-shaped drug holding opening 1 enters the air inlet channel 6 with the airflow,→the large inside diameter vortex chamber 7,→the small inside diameter air inlet channel 18,→the large inside diameter vortex chamber 17,→the small inside diameter air outlet channel 8,→mouthpiece 9→the oral cavity. In a word, the air enters the user's mouth from the funnel-shaped drug holding opening 1. Although the inner capacity of the vortex passages is only about 1.8 cube cm, the vortex has come into being for twice, which could bring the medicinal powder evenly suspending in the airflow to form a medicinal powder aerosol. Hence, the drug powder will be widely delivered to the lower respiratory tract and the alveolus with the breathing in at the earliest time.

As mentioned above, the core technique of this invention is to aerosolize the dry powder so as to increase the inhalation rate. Firstly, the application of the vortex passages in breathe-in channel is found out, and the change of the inside diameter of the passages forms a unit of vortex passage, which is of simple structure but with good effect in dispersing dry powder. The greater the ratio of the transect area of the vortex chamber to the transect area of the air inlet or outlet channels in the vortex passages is, the more important role it plays in dispersing the dry powder. The vortex passages can be connected in series or in parallel, or partly in series and partly in parallel as well, and each connecting way mentioned above will play a more significant role in dispersing the dry powder. Because of the simple structure, this invention can easily fabricated, and it smoothes the way to dismount for cleaning and sterilizing after every use, so as to prevent from cross inflection; and it is a key link for increasing the inhalation rate and case fatality rate. Secondly, the inhaler has a long mouthpiece connector and external casing with the suction mouth towards the throat directly, decreasing the adhering of the powder to the oral cavity and tongue and enabling more powder to be breathed into the respiratory tract directly. Thirdly, the bottom of the drug holding opening connects with the vortex passage directly, helping the air to push more dispersed dry powder into the bronchioles or even the alveolus. This invention also assembles a valve plate at the air inlet, simple as which might be, it cracks the hard nut of long standing as the powder will easily be blown out from the inhaler. And the technical feature as the air inlet channel to be composed by a few small gaps to filter the foreign matter in the air distinguishes it from other current inhalers in structures, and it can be used for many different powder inhalations.

The of this invention are disclosed with specific examples thereof, it is evident that many variations and modifications will be apparent to those skilled in the art. Accordingly, it is intended to embrace all such variations and modifications and that fall within the spirit and scope of the invention.

The invention claimed is:

1. A dry powder aerosolized inhaler comprising:
a main body (11); and
a mouthpiece connector (12) connecting to the main body, wherein a funnel-shaped drug holding opening (1) in the main body (11) is connected to an air inlet (4) of the main body configured to provide unidirectional air flow towards the drug holding opening and to resist air flow out through the air inlet, and the drug holding opening is further connected to and decreases in diameter towards a vortex passage on a side opposite to the connection to the air inlet, and
wherein the vortex passage has only one air inlet channel (6) having a first inside diameter, a vortex chamber (7) having an inside diameter greater than the first inside diameter, and one air outlet channel (8) having a minimum inside diameter that is not greater than the first inside diameter of the air inlet channel, wherein the air outlet channel is further connected to a mouthpiece (9) on the mouthpiece connector (12).

2. The dry powder aerosolized inhaler of claim 1, wherein above the drug holding opening (1), the main body (11) comprises a cover slab (2).

3. The dry powder aerosolized inhaler of claim 2, wherein the cover slab (2) has openings.

4. The dry powder aerosolized inhaler of claim 2, wherein the air inlet (4) is connected with the funnel-shaped drug holding opening (1) through an air inlet channel (5).

5. The dry powder aerosolized inhaler of claim 4, wherein the main body (11) comprises a single direction valve plate (3) at the air inlet (4), and the air inlet channel (5) connecting the air inlet (4) with the funnel-shaped drug holding opening (1) comprises several small gaps of about 1 mm width to filtrate foreign matter in the air.

6. The dry powder aerosolized inhaler of claim 1, comprising more than one said vortex passage, connected in series, or in parallel, or partly in series and partly in parallel, wherein each vortex passage has only one air inlet channel and one air outlet channel.

7. The dry powder aerosolized inhaler of claim 6, wherein the air inlet channel (6) has one end that connects with the vortex chamber (7) and another end that connects with the drug holding opening (1); the vortex chamber (7) directly connects with the air outlet channel (8) or with a small inside diameter air inlet channel of a neighbor vortex passage; and following this rule, until the small inside diameter air outlet channel in a last one of the vortex passages connects with the mouthpiece (9).

8. The dry powder aerosolized inhaler of claim 7, wherein a joint between the vortex chamber (7) and the air inlet channel (6) is a structure of gradual change or of abrupt change.

9. The dry powder aerosolized inhaler of claim 1, wherein the mouthpiece connector (12) comprises an external casing (10).

10. The dry powder aerosolized inhaler of claim 9, comprising a small protuberance at a bottom side of the external casing (10), which helps fix the external casing (10) when interlocking with a small whorl on the main body (11).

* * * * *